(12) United States Patent
Dupont et al.

(10) Patent No.: US 7,883,475 B2
(45) Date of Patent: Feb. 8, 2011

(54) MANIPULATORS EMPLOYING MULTIPLE DEFORMABLE ELONGATE MEMBERS

(75) Inventors: Pierre E. Dupont, Wellesley, MA (US); Matthew C. Heverly, Pasadena, CA (US)

(73) Assignee: Trustees of Boston University, Boston, MA (US)

( * ) Notice: Subject to any disclaimer, the term of this patent is extended or adjusted under 35 U.S.C. 154(b) by 168 days.

(21) Appl. No.: 12/117,101

(22) Filed: May 8, 2008

(65) Prior Publication Data

US 2008/0215067 A1 Sep. 4, 2008

Related U.S. Application Data

(63) Continuation of application No. PCT/US2006/043842, filed on Nov. 8, 2006.

(60) Provisional application No. 60/734,619, filed on Nov. 8, 2005.

(51) Int. Cl.
*A61M 25/01* (2006.01)
(52) U.S. Cl. ............... 600/585; 604/264; 604/523; 604/528; 604/530; 606/108
(58) Field of Classification Search ............... 700/245, 700/246, 247, 257; 604/22, 96, 164.13, 604.01, 604/515, 284, 523, 524, 93.01, 158, 164.01, 604/164.11, 264, 528, 530; 607/101, 104; 606/41, 42, 45, 95.04, 142, 147, 151, 164.13, 606/194, 219, 108; 600/585
See application file for complete search history.

(56) References Cited

U.S. PATENT DOCUMENTS 6,572,593 B1 * 6/2003 Daum .................... 604/264

2003/0144657 A1 * 7/2003 Bowe et al. .................... 606/41
2004/0019359 A1 * 1/2004 Worley et al. ............... 606/129
2004/0133168 A1 * 7/2004 Salcudean et al. ...... 604/164.13

(Continued)

FOREIGN PATENT DOCUMENTS

DE 4223897 A1 1/1994

OTHER PUBLICATIONS

Ebrahimi et al., "Handheld Steerable Needle Device," Medical Image Computing and Computer Assisted Intervention, 2003, pp. 223-230.

(Continued)

*Primary Examiner*—Khoi Tran
*Assistant Examiner*—Spencer Patton
(74) *Attorney, Agent, or Firm*—BrainwoodHuang

(57) ABSTRACT

A manipulator is configured with three or more substantially concentric, elongate members configured such that relative rotation and translation of the elongate members adjusts both the spatial position and orientation of the distal end of the manipulator and the spatial positioning of the manipulator along its length. In one arrangement, the elongate members are pre-curved such that the distal end portions of the elongate members have generally arcuate shapes in a resting state. When the three elongate members are combined in a substantially concentric manner, the overall shape of the manipulator is a composite of the individual elongate member shapes. Varying the relative translation and rotational orientation of the component elongate members achieves a family of resulting manipulator shapes as well as a desired spatial position and orientation of the distal end portion of the manipulator.

11 Claims, 11 Drawing Sheets

U.S. PATENT DOCUMENTS

| | | | |
|---|---|---|---|
| 2005/0070844 A1* | 3/2005 | Chow et al. | 604/95.04 |
| 2005/0267495 A1* | 12/2005 | Ginn et al. | 606/151 |
| 2006/0212071 A1* | 9/2006 | Ginn et al. | 606/219 |
| 2006/0224118 A1* | 10/2006 | Morris et al. | 604/164.01 |
| 2009/0270835 A1* | 10/2009 | Kushner | 604/515 |

OTHER PUBLICATIONS

Froehlich et al., "New Cannula for Endo-Scopic Reflux Operation in Children and Infants," J. Endourol., Apr. 1994, 8(2), pp. 131-132.

Furusho et al., "Curved Multi-Tube Systems for Fetal Blood Sampling and Treatments of Organs Like Brain and Breast," Journal of Computer Assisted Radiology and Surgery, 2006, pp. 223-226.

Furusho et al., "Development of a Curved Multi-Tube (CMT) Catheter for Percutaneous Umbilical Blood Sampling and Control Methods of CMT Catheters for Solid Organs," Proceedings of the IEEE International Conference on Mechatronics & Automation, Niagra Falls, CA, Jul. 2005, pp. 410-415.

Li et al., "Design of Continuous Backbone, Cable-Driven Robots," ASME Journal of Mechanical Design, vol. 124, 2002, pp. 265-274.

Loser, "A New Robotic System for Visually Controlled Percutaneous Interventions Under X-ray Fluoroscopy of CT-imaging," Dr. Ing. Dissertation, Microsystems Technology, U. Freiburg, Germany, ISBN 978-3-8325-0845-6, 2005.

Sinaan et al., "A Dexterous System for Laryngeal Surgery—Multi-Backbone Bending Snake-Like Slaves for Teleoperated Dexterous Surgical Tool Manipulation," IEEE International Conference on Robotics and Automation, New Orleans, 2004, pp. 351-357.

* cited by examiner

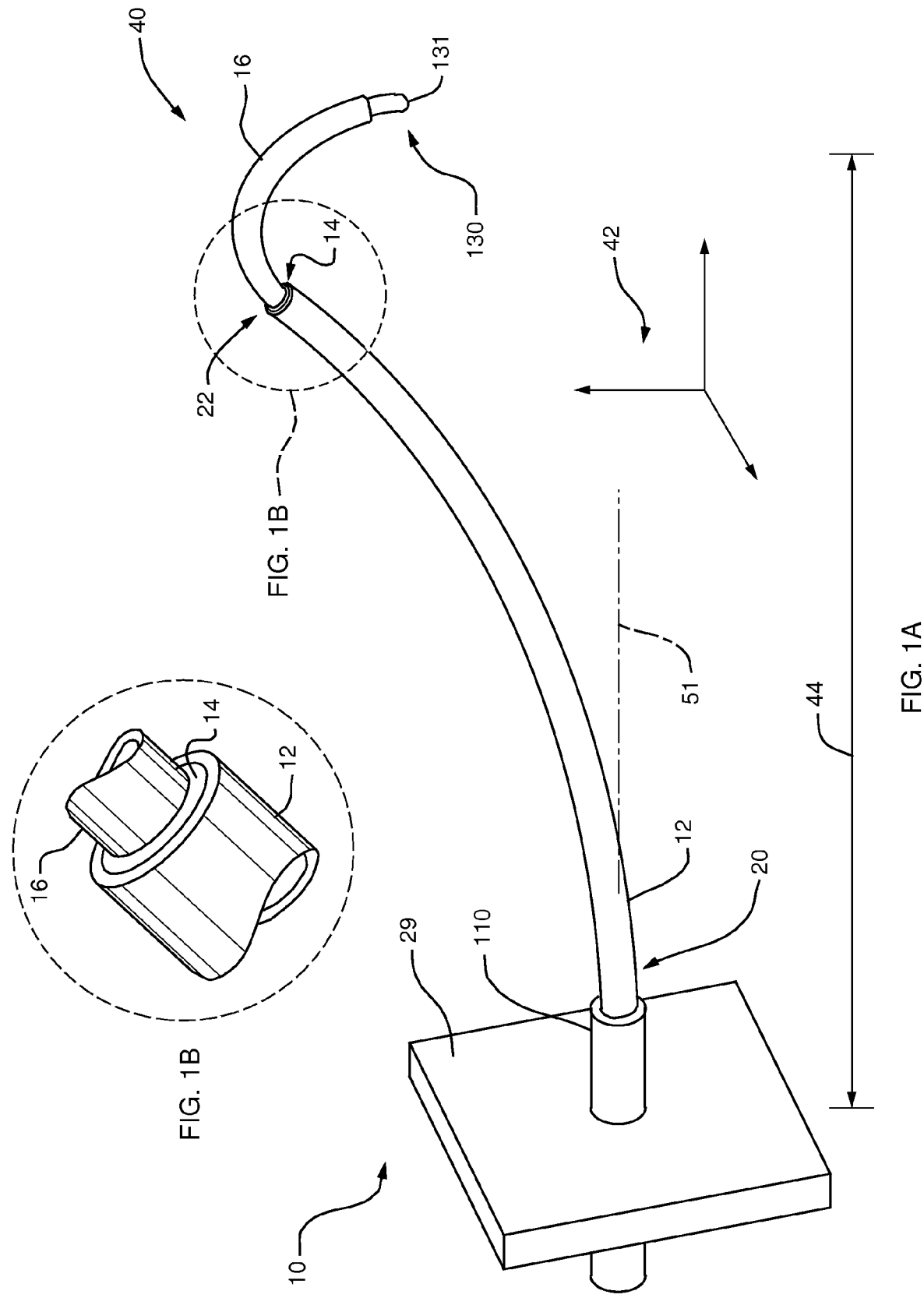

US 7,883,475 B2

MANIPULATORS EMPLOYING MULTIPLE DEFORMABLE ELONGATE MEMBERS

STATEMENT OF FEDERAL RIGHTS

This invention was made with Government support under Contract Numbers HL073647 and EB003052 awarded by the National Institutes of Health. The Government has certain rights in the invention.

BACKGROUND

Minimally invasive medical procedures involve the delivery and manipulation of drugs, tools and prosthetic devices inside the body while minimizing or avoiding damage to surrounding tissue structures. Entry to the body may be percutaneous or through an orifice. The surgical target may lie in the interior of a solid tissue structure or inside a body cavity. In many cases, the need arises during insertion to steer along three-dimensional curves through tissue to avoid bony or sensitive structures (percutaneous procedures), or to follow the interior contours of a body orifice (e.g., the nasal passages) or body cavity (e.g., the heart).

Some procedures, such as drug delivery, do not require articulation of the instrument's distal tip while for others it is necessary to control the position and orientation of the distal tip while holding relatively immobile the proximal inserted length. An example of the latter case arises in the navigation and articulation of interventional tools in minimally invasive intracardiac reconstructive surgery and arrhythmia management. Minimally-invasive beating-heart repair of congenital cardiac defects in children can require the use of instruments with diameters of 3-5 mm while the repair of fetal defects in utero can require the use of instruments having diameters of one millimeter or less.

The instruments used in minimally invasive procedures typically fall into one of three general categories. The first category includes straight flexible needles which are used for percutaneous procedures in solid tissue. Steering of the straight flexible needles along a curved insertion path is achieved by applying lateral forces at the needle base or tip as the practitioner inserts and advances the needle into the tissue. The lateral forces cause the partially inserted needle to flex in a desired steering direction. Base steering is accomplished by lateral displacement or rotation of the uninserted portion of the needle while tip steering is accomplished using either a beveled or curved tip, both of which produce a lateral steering force in the direction of the bevel or curve. The steering direction is adjusted by rotating the needle about its axis. Since the needle is initially straight, both base and tip steering methods rely on tissue reaction forces to flex the needle along a curved insertion path. Consequently, these instruments possess no ability to produce lateral tip motion without further penetration into solid tissue.

The second category of instruments includes a straight, fairly rigid shaft with an articulated tip-mounted tool (e.g., forceps). Both hand-held and robotic instruments of this type are in common use for minimally invasive access of body cavities (e.g., chest or abdomen). The shaft must follow a straight-line path from the entry point to the body to the surgical site. Lateral motion of the tip depends on pivoting the straight shaft about a fulcrum typically located at the insertion point into the body. This pivoting motion produces tissue deformation proportional to the thickness of tissue from the entry point to the body cavity.

The third category of instruments includes elongated, steerable devices, such as multi-stage micro-robot devices, which are typically used for entry through a body orifice, and steerable catheters, which are most often used for percutaneous access of the circulatory system. Multi-stage micro-robot devices are typically mounted at the distal end of a rigid shaft and include a flexible backbone having a series of regularly spaced platforms that are interconnected by hinges and attached to a base by wires. User actuation of the wires causes the backbone to bend. These devices are typically sufficiently rigid to support their own weight as well as to apply appreciable lateral forces to the surrounding tissue. In contrast, steerable catheters include an elongate member of sufficient flexibility so as to conform to the curvature of the vessel through which it is advanced. Steering is achieved using one or more wires attached to the distal end of the elongate member disposed along the catheter's length. User actuation (e.g., pulling) of the wires causes the distal portion of the elongate member to flex in one or more directions. An alternate approach to catheter steering for navigating branches in the circulatory system involves the use of a guide wire. After inserting the flexible catheter up to the branch point, the guide wire, with a curvature preset at its distal end, is inserted through the catheter until its curved portion is extended beyond the distal end of the catheter and into the desired branch vessel. At this point, pushing on the catheter from the base causes its distal end to follow the wire into the branch vessel.

SUMMARY

Conventional approaches to adjusting the position of an elongate member within a tissue region or body cavity suffer from a variety of deficiencies.

As described above, practitioners steer straight, flexible needles within tissue by applying lateral forces at the base or tip of the flexible needle as the practitioner inserts and advances the needle into the tissue. However, the interaction between the conventional flexible needle and the tissue is used to control the shape of the needle during use. For example, the interaction between the beveled tip of the needle and the tissue acts to steer the needle along a particular path while tissue reaction forces operate on the flexible needle during insertion and cause the needle to bend in a particular direction.

Conventional handheld and robotic minimally invasive instruments include a rigid straight shaft with limited articulation present only at the distal end. In consequence, the instrument must follow a straight-line path from the incision location to the surgical site inside the body. Furthermore, lateral motion of the tool located at the instrument's distal end requires pivoting about a point along the shaft. The tissue deformation produced by such motion limits the locations within the body that can be accessed and operated on by instruments of this type.

With respect to the multi-stage micro-robot devices, such devices do provide a level of articulation to otherwise rigid shafts. However, the multi-stage micro-robot devices include multiple platforms, hinges, and wires that, taken collectively, form a relatively bulky device (e.g., having an outer diameter of about 4 mm). As such, the multi-stage micro-robot devices cannot be utilized in all percutaneous procedures, such as for the repair of fetal defects in utero. With respect to the steerable catheters, the catheters are successful at navigating existing channels in tissue (e.g., arteries and veins). However, the steerable catheter itself typically does not have the flexural rigidity to penetrate appreciably into tissue. The steerable catheter typically must be used in conjunction with a cannula for percutaneous insertion into a tissue site.

Embodiments of the present invention relate to a manipulator having three or more substantially concentric, elongate members configured such that relative rotation and/or translation of the elongate members adjusts both the spatial position and orientation of the distal end of the manipulator and the spatial positioning of the manipulator along its length. In one arrangement, the elongate members are pre-curved such that the distal end portions of the elongate members have generally arcuate shapes in a resting state. When the three elongate members are combined in a substantially concentric manner, the overall shape of the manipulator is a composite of the individual elongate member shapes. Varying the relative translation and rotational orientation of the component elongate members achieves a family of resulting manipulator shapes as well as a desired spatial position and orientation of the distal end portion of the manipulator. In addition to the pre-curved geometric shape of the elongate members affecting the positioning of the manipulator, the relative stiffness of the elongate members determines the relative contribution of each elongate member to the final shape of the manipulator. When the stiffness of one elongate member is much greater than the other, the resulting shape of the manipulator depends upon the linear actuation of the elongate member having the lesser stiffness relative to the elongate member having the greater stiffness. When the relative stiffness of the elongate members is substantially equal, the resulting shape of the manipulator depends on both the relative rotation and the relative linear actuation of the elongate members.

In one embodiment, the manipulator is configured as a needle manipulator for use in percutaneous procedures. In use, the needle manipulator allows percutaneous insertion of millimeter or micrometer scale tools and devices into tissue and allows the operator to steer the tools along a curved path to a desired surgical site, as caused by relative rotation and translation of the manipulator elongate members. As such, the needle manipulator does not rely on tissue interaction to determine its geometric configuration and does not require a special control device along its length to steer or control positioning of the distal end of the manipulator. Also, with such steering capability, the needle manipulator can avoid obstacles, such as bone or delicate tissue, as the distal end of the needle manipulator is advanced to a surgical site.

In one embodiment, a manipulator comprises at least three elongate members disposed in a moveable relationship and in a substantially concentric relationship relative to each other. At least one elongate member of the at least three elongate members is configurable, within an elastic range, between a rest configuration in which at least a portion of the at least one elongate member of the at least three elongate members assume a generally arcuate position relative to a reference axis and a non-rest configuration in which at least a portion of the at least one elongate members of the at least three elongate members assume a generally extended position relative to the reference axis. The at least three elongate members are configured such that relative displacement of the at least three elongate members adjusts a spatial position of a distal end of the manipulator. In one arrangement, a first set of elongate members of the at least three elongate members are configured to be positioned between the non-rest configuration and the rest configuration in response to relative rotation between a first elongate member of the first set of elongate members and a second elongate member of the first set of elongate members about the reference axis. A second set of elongate members of the at least three elongate members are configured to be positioned between the non-rest configuration and the rest configuration in response to relative translation between a first elongate member of the second set of elongate members and a second elongate member of the second set of elongate members along the reference axis.

One embodiment relates to a method for positioning a distal end of a manipulator having at least three elongate members disposed in a moveable relationship and in a substantially concentric relationship relative to each other. The method includes, with respect to a first set of elongate members of the at least three elongate members, displacing a first elongate member of the first set of elongate members relative to a second elongate member of the first set of elongate members to adjust a spatial position of a distal end of the manipulator. The method includes, with respect to a second set of elongate members of the at least three elongate members, displacing a first elongate member of the second set of elongate members relative to a second elongate member of the second set of elongate members along the reference axis to adjust a spatial position of a distal end of the manipulator.

One embodiment relates to a method for positioning a distal end of a needle apparatus within a tissue. The method includes inserting a distal end portion of the needle apparatus into a tissue region, the needle apparatus having at least three elongate members disposed in a moveable relationship and in a substantially concentric relationship relative to each other, each elongate member of the at least three elongate members having a proximal end portion, a distal end portion, and a lumen extending along a longitudinal axis. The method includes, with respect to a first set of elongate members of the at least three elongate members, displacing a first elongate member of the first set of elongate members relative to a second elongate member of the first set of elongate members to adjust a spatial position of a distal end of the needle manipulator. The method includes, with respect to a second set of elongate members of the at least three elongate members, displacing a first elongate member of the second set of elongate members relative to a second elongate member of the second set of elongate members along the reference axis to adjust a spatial position of a distal end of the needle manipulator.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 1A illustrates an example of a manipulator.

FIG. 1B is a close-up view of a portion of the manipulator of FIG. 1A.

DETAILED DESCRIPTION

Figure 1C:
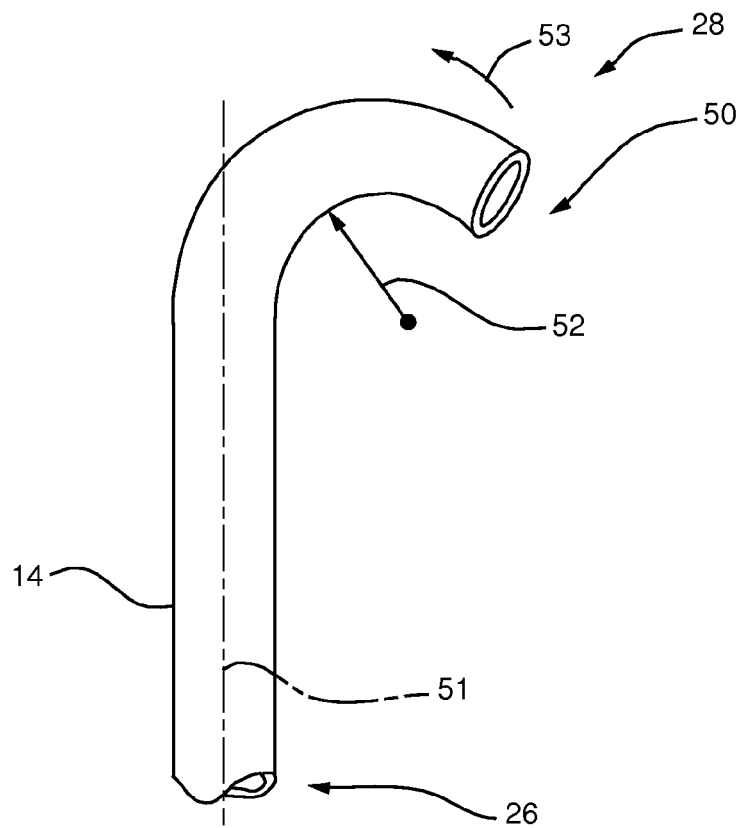
FIG. 1C illustrates a pre-curved elongate member of the manipulator of FIG. 1A in a rest state.

Embodiments of the present invention relate to a manipulator having three or more substantially concentric, elongate members configured such that relative rotation and/or translation of the elongate members adjusts both the spatial position and orientation of the distal end of the manipulator and the spatial positioning of the manipulator along its length. In one arrangement, the elongate members are pre-curved such that the distal end portions of the elongate members have generally arcuate shapes in a resting state. When the three elongate members are combined in a substantially concentric manner, the overall shape of the manipulator is a composite of the individual elongate member shapes. Varying the relative translation and rotational orientation of the component elongate members achieves a family of resulting manipulator shapes as well as a desired spatial position and orientation of the distal end portion of the manipulator. In addition to the pre-curved geometric shape of the elongate members affecting the positioning of the manipulator, the relative stiffness of the elongate members determines the relative contribution of each elongate member to the final shape of the manipulator. When the stiffness of one elongate member is much greater than the other, the resulting shape of the manipulator depends upon the linear actuation of the elongate member having the lesser stiffness relative to the elongate member having the greater stiffness. When the relative stiffness of the elongate members is substantially equal, the resulting shape of the manipulator depends on both the relative rotation and the relative linear actuation of the elongate members.

FIG. 1A illustrates an example embodiment of a manipulator 10 having at least three elongate members. As illustrated, the manipulator 10 has a first elongate member 12, a second elongate member 14, and a third elongate member 16 disposed in a moveable relationship, and in a substantially concentric relationship, relative to each other. In one arrangement, the elongate members 12, 14 are configured as concentrically disposed tubes. For example, with reference to FIG. 4A, the first elongate member 12 defines a first elongate member lumen 18 having a substantially circular cross-sectional shape and that extends between a proximal end portion 20 and a distal end portion 22 with the second elongate member 14 being disposed within the first elongate member lumen 18. The second elongate member 14 defines a second elongate member lumen 24 having a substantially circular cross-sectional shape and that extends between a proximal end portion 26 and a distal end portion 28 with the third elongate member 16 being disposed within the second elongate member lumen 24. In one arrangement, the manipulator 10 includes a base or housing 29 that supports or carries the elongate members 12, 14, 16 where the elongate members 12, 14, 16 are moveable (e.g., rotatable and translatable) relative to the base 29.

In one arrangement, contact among the outer and inner walls of the elongate members 12, 14, 16 maintains the substantially concentric positioning of the elongate members 12, 14, 16. For example, with reference to FIG. 4A, contact between an inner lumen wall 30 of the first elongate member 12 and an outer wall 32 of the second elongate member 14 and contact between an inner lumen wall 34 of the second elongate member 12 and an outer wall 36 of the third elongate member 14 aligns the elongate members in a substantially concentric manner.

Returning to FIG. 1A, a variety of materials can be used to form the elongate members 12, 14, 16. In one arrangement, one or more of the elongate members 12, 14, 16 are formed from a super-elastic material, such as a nickel titanium alloy (e.g., Nitinol), from an elastic material, such as plastic, or from a relatively stiff material, such as stainless steel. While the material composition and properties of the elongate members 12, 14, 16 can be constant along a length of the elongate members 12, 14, 16, in one arrangement, the material composition of one or more of the elongate members 12, 14, 16 varies along its length. For example, one or more of the elongate members 12, 14, 16 can be formed from a stainless steel material between a proximal end portion and a distal end portion of the elongate member while having a Nitinol material disposed at the distal end portion of the elongate member.

The geometric configuration of the elongate members 12, 14, 16 can affect both the spatial position and orientation of a distal end 40 of the manipulator 10, relative to a reference coordinate system 42 and the spatial positioning of the manipulator 10 (e.g., along its length 44) relative to the reference coordinate system 42. In one embodiment, each of the elongate members 12, 14, 16 is formed as having a preset curved shape. Taking the second elongate member 14 as an example, as illustrated in FIG. 1C, the second elongate member 14 is formed such that, in a resting position (e.g., subject to minimal external forces) at least a portion 50 of the second elongate member 14 assumes a generally arcuate shape 50 having a radius of curvature 52 relative to a reference axis 51. As shown, the arcuately shaped portion 50 is disposed at a distal end portion 28 of the second elongate member 14. However, one of ordinary skill in the art will understand that the arcuately shaped portion 50 can extend along a length of the second elongate member 14, from the proximal end 26 to the distal end 28.

Figure 5:
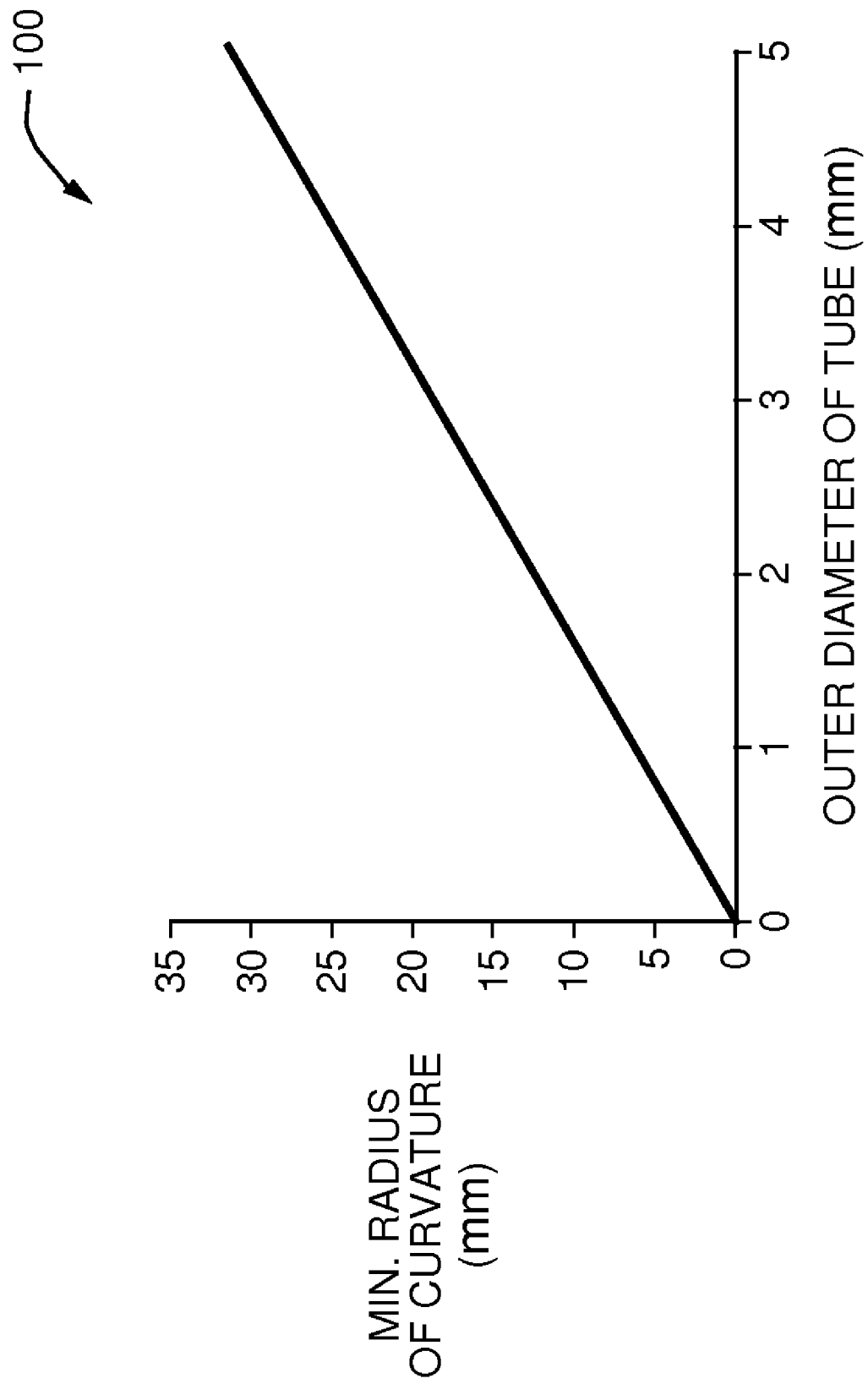
FIG. 5 is a graph illustrating the relationship between the radius of curvature and elongate member outer diameter.

When forming a particular resting radius of curvature in an elongate member, designers take several variables into consideration. For example, FIG. 5 is a graph 100 that illustrates the relationship between radius of curvature and elongate member (e.g., tube) outer diameter for a Nitinol material. As shown, the minimum achievable radius of curvature of an elongate member is a function of elongate member outer diameter. Therefore, the smaller the outer diameter of the elongate member, the smaller the radius of curvature achievable in the elongate member.

Figure 1D:
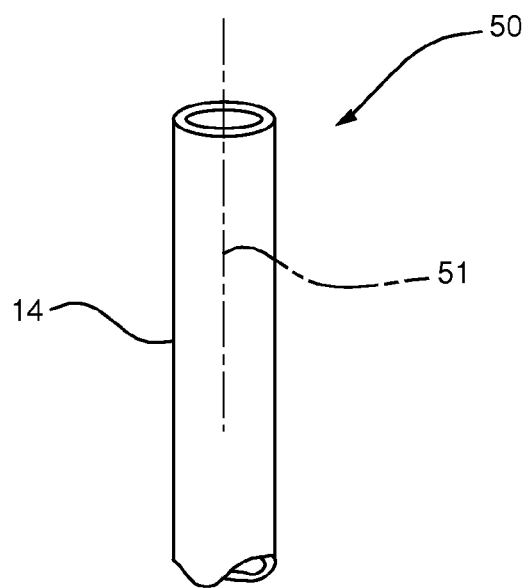
FIG. 1D illustrates the pre-curved elongate member of FIG. 1C in a non-rest state.

The elongate members 12, 14, 16 hold or maintain the generally arcuate shape or position while in a rest configuration, such as when no outside forces act upon the elongate members 12, 14, 16. When an outside force is applied to the second elongate member 14, the outside force can position the elongate member 14 in an extended position (e.g., non-rest configuration), as illustrated in FIG. 1D. For example, as indicated in FIG. 1C, application of an outside bending force 53 on the second elongate member 14 substantially straightens the arcuately shaped portion 50, as shown in FIG. 1D, such that a longitudinal axis of the second elongate member 14 is substantially parallel to the reference axis 51. A curved member can also have its curvature increased by such an outside bending force, as discussed below with reference to FIG. 3A for example.

When one pre-curved elongate member is disposed within another pre-curved elongate member, both elongate members are forced to conform to a mutual final curvature. As such, the elongate members change position between the rest configuration (e.g., at least a portion of the elongate member assumes a generally arcuate shape) and the non-rest configuration (e.g., at least a portion of the elongate member assumes a generally extended shape). By translating and rotating one elongate member with respect to the other, both the final curvature as well as the overall length of the manipulator 10 can be varied to adjust a position of the distal end 40 of the manipulator 10 relative to the reference coordinate system 42 and relative to the reference axis 51.

For example, with reference to FIG. 1A, each of the first and second elongate members 12, 14 are configured as having a preset curved shape. In the case where the first and second elongate members 12, 14 are rotated and translated relative to each other, the first and second elongate members 12, 14 are positioned between the rest configuration, as shown in FIG. 1C and the non-rest configuration (e.g., extended position) as shown in FIG. 1D, thereby causing the manipulator 10 to conform to a final, mutual curvature, such as shown in FIG. 1A. The rotation and translation of the pre-curved elongate members 12, 14, therefore, changes the spatial positioning of the distal end portion 40 of the manipulator 10 (e.g., the distal end portions 22, 28 of the first and second elongate members 10) relative to the reference coordinate system 42 and relative to the reference axis 51. As such, by rotating and translating the first and second elongate members 12, 14, a user can adjust the spatial positioning of the distal end portion 40 of the manipulator 10 in order to steer and deliver the distal end portion 40 to a particular spatial location.

While the relative positioning of the pre-curved shapes of the elongate members 12, 14, 16 can adjust the curvature of the manipulator 10, other factors can also affect the positioning of the manipulator 10 relative to the reference coordinate system 42. For example, the relative bending stiffnesses of a set of the elongate members 12, 14, 16 can affect the positioning of the manipulator 10. The bending stiffness of an elongate member is defined as the modulus of elasticity of the material forming the elongate member multiplied by the cross-sectional moment of inertia of the elongate member. In one arrangement, the relative bending stiffnesses of a set of the elongate members 12, 14, 16 can define a dominating stiffness relationship where the bending stiffness of one elongate member is much larger than that of the other (e.g., the stiffness ratio approaches infinity). For example, a stiffness ratio of 10:1 between two elongate members can represent a practical lower bound for a dominating stiffness relationship in some applications. Alternatively, it may be that the combined stiffness of two tubes (e.g., 12 and 14) should be much larger than that of the third tube (e.g. 16). In another arrangement, the relative bending stiffnesses of a set of the elongate members 12, 14, 16 can define a balanced stiffness relationship where the stiffnesses of a set of elongate members are substantially equal (e.g., the stiffness ratio equals approximately 1). Balanced and dominating stiffness relationships represent the two limits of relative stiffness (stiffness ratio equals approximately 1 for balanced; stiffness ratio approaches infinity for dominating case). As such, manufacturing of manipulators 10 from combinations of these cases are useful for both expository and practical reasons. One of ordinary skill in the art will understand, however, that the elongate members 12, 14, 16 can be configured as having stiffnesses that are classified as neither balanced nor dominating. Description of the concepts of a dominating stiffness elongate member set and a balanced stiffness elongate member set is provided below.

Figure 2A:
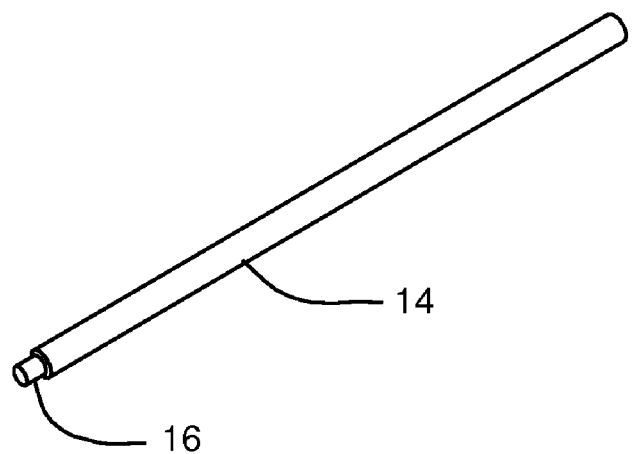
FIG. 2A illustrates a dominating stiffness elongate member pair in a retracted configuration.
Figure 2B:
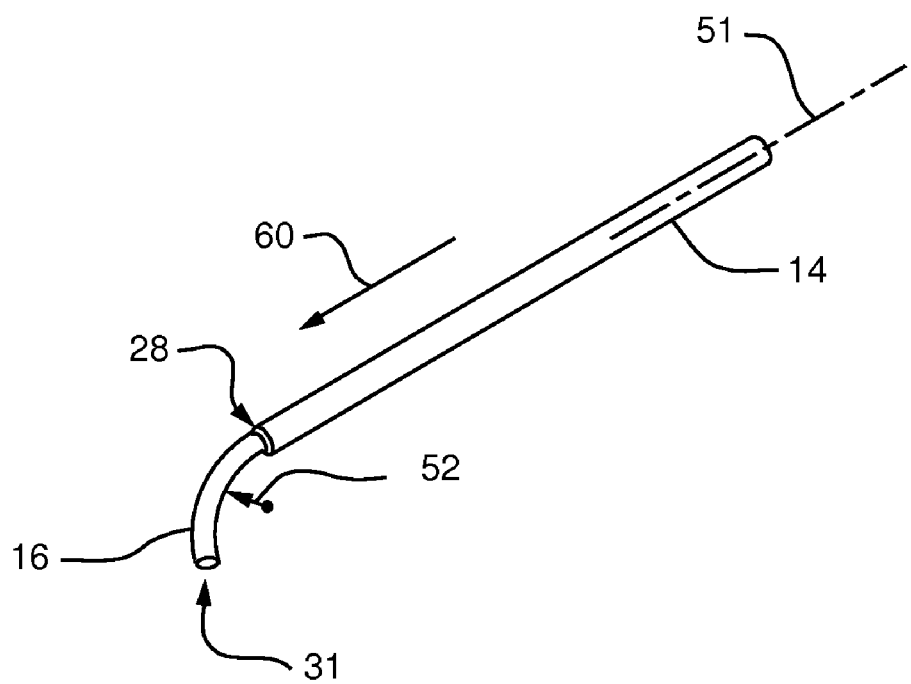
FIG. 2B illustrates the dominating stiffness elongate member pair of FIG. 2A in an extended configuration.

FIGS. 2A and 2B illustrate the concept of a dominating stiffness elongate member set. When the bending stiffness of one elongate member is much larger than that of the other, the set of concentric elongate members conforms to the curvature of the stiffer elongate member. When the more flexible elongate member is translated relative to the stiffer elongate member, as the more flexible elongate member extends beyond a distal end of the stiffer elongate member, the extended portion relaxes to its original preset curvature.

For example, with reference to FIG. 2A, assume the second elongate member 14 is formed of a relatively stiff material having a generally elongate shape while the third elongate member 16 is formed of a relatively compliant material having a preset curved shape. In the case where the third elongate member 16 is disposed within the second elongate member 14, the bending stiffness of the second elongate member 14 dominates that of the third elongate member 16. The second elongate member 14 therefore applies an outside force to the third elongate member 16 and positions the third elongate member 16 in an extended position. As shown in FIG. 2B, as the third elongate member 16 translates along a direction 60 relative to the second elongate member 14, a distal portion 31 of the third elongate member 16 extends beyond the distal end portion 28 of the second elongate member 14 and relaxes to a resting, curved shape, relative to the reference axis 51. The curvature of the third elongate member 16 can be substantially constant as shown or can vary over its extended length Generally, the dominating stiffness elongate member set has two independent degrees of freedom which determine the overall shape and relative locations of the proximal and distal ends of the set: a first degree of freedom related to the relative linear translation of the set relative to the reference axis 51 and a second degree of freedom related to the relative rotation of the elongate members 14, 16 about the reference axis 51.

Figure 3A:
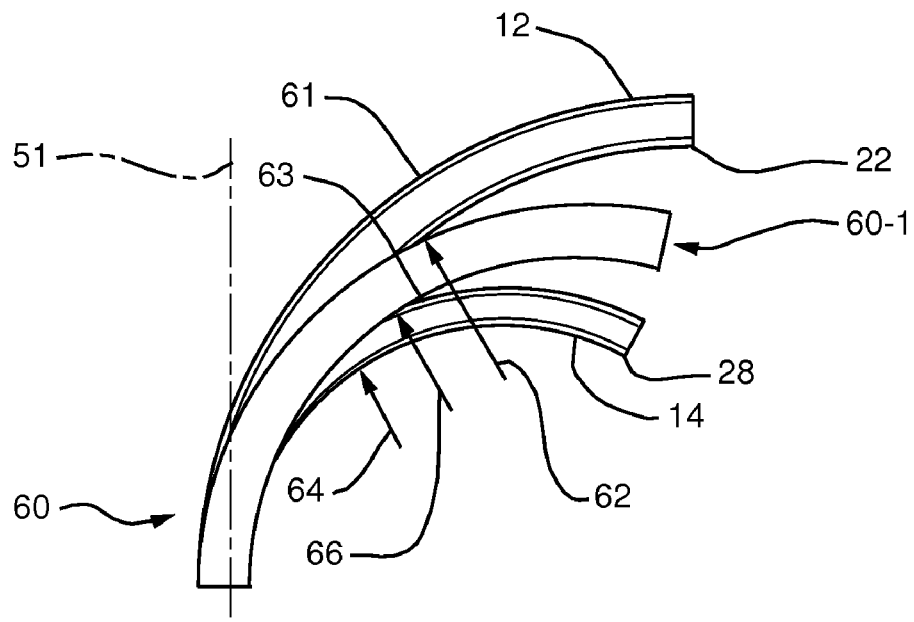
FIG. 3A illustrates a resulting geometric configuration of a balanced stiffness elongate member set where the curvatures of the elongate members of the balanced stiffness elongate member set are substantially aligned.
Figure 3B:
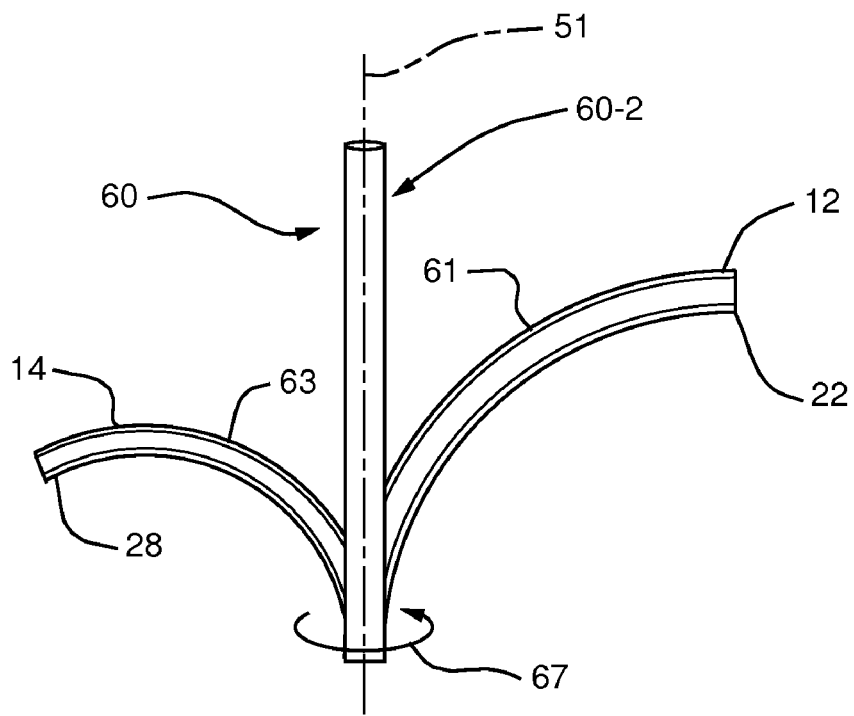
FIG. 3B illustrates a resulting geometric configuration of the balanced stiffness elongate member set of FIG. 3A where the curvatures of the elongate members of the balanced stiffness elongate member set are substantially opposed.

FIGS. 3A and 3B illustrate the concept of a balanced stiffness elongate member set. In the case where preset curved elongate members have substantially equal stiffnesses, when one elongate member is disposed within another, the curvatures of the elongate members interact with each other and combine to form a single, resultant curvature 60.

For example, as shown in FIG. 3A, the first elongate member 12, in a rest configuration, defines a first member curvature 61 having a first member radius 62 and the second elongate member 14, in a rest configuration, defines a second member curvature 63 having a second member radius 64 that is smaller than the first member radius 62. When the first and second elongate members 12, 14 are disposed in a concentric relationship such that the individual curvatures 61, 63 of the elongate members 12, 14 are substantially aligned and the associated distal end portions 22, 28 are oriented in substantially the same direction (e.g., point to the right hand side of the page, as illustrated) the resultant curvature 60-1 of the elongate member set has a resultant radius of curvature 66 that is greater than the second member radius 64 and that is less than the first member radius 62. In the case where the curvatures of the elongate members 12, 14 are aligned, as shown in FIG. 3A, the resultant curvature 60-1 provides the maximum curvature of the balanced stiffness elongate member set.

As indicated in FIG. 3B, relative rotation of the elongate members 12, 14 of FIG. 3A, causes the combined curvature 60 to vary. For example, as the first elongate member 12 and the second elongate member 14 of FIG. 3A rotate relative to each other about the reference axis 51, interaction between the first and second elongate members 12, 14 causes the resultant radius of curvature 66 to increase. As the first and second elongate members 12, 14 are further rotated 67 such that the unstressed curvatures 61, 63 of the elongate members 12, 14 oppose each other and the associated distal end portions 22, 28 orient in substantially opposing directions, as indicated in FIG. 3B, the resultant curvature 60-2 of the elongate member set is substantially aligned with the reference axis 51. As such, the balanced stiffness elongate member set 12, 14 is positioned in a maximally extended position. A second degree of freedom of the balanced stiffness elongate member pair can be achieved by rotating of the balanced stiffness elongate member set 12, 14 about the base 29, as illustrated in FIG. 1A. One of ordinary skill in the art will understand that the initial curvatures of the balanced stiffness elongate member pair can be constant over their length, as shown in FIGS. 3A and 3B, or can be variable.

Returning to FIG. 1A, the manipulator 10, in one embodiment, is formed from a combination of elongate members 12, 14, 16. With such configurations, the curvature of the manipulator 10 can be mathematically modeled to predict the final curvature of the manipulator 10. While a variety methods can be used for predicting the final curvature of an arbitrary number of elongate members, the following analysis represents one example method. In this example method, it is assumed that each elongate member 12, 14, 16 has piecewise constant curvature and that bending stresses remain elastic. While the actual loading between elongate members consists of forces distributed along their common boundary, it is assumed here that each member 12, 14, 16 experiences pure bending. This approximation implies that the elongate members 12, 14, 16 apply bending moments to each other which are constant along those portions of their common length in which each member 12, 14, 16 is of constant curvature. It is assumed that these moments are generated over negligibly short lengths at the ends of each constant curvature section. Finally, it is assumed that the elongate members 12, 14, 16 can be approximated as rigid in torsion. The validity of this assumption depends on the design of the manipulator 10. It is employed in this example because it permits a particularly simple solution that is computationally efficient to implement.

Combining these assumptions with the Euler-Bernoulli beam model permits direct calculation of the resulting curvature of each length of a manipulator 10 in which the individual elongate members 12, 14, 16 have constant curvature. In this way, elongate members 12, 14, 16 of piecewise constant curvature combine to form manipulators 10 of piecewise constant curvature whose shape can be computed without resorting to integrating differential equations or solving numerical optimization problems.

Figure 8A:
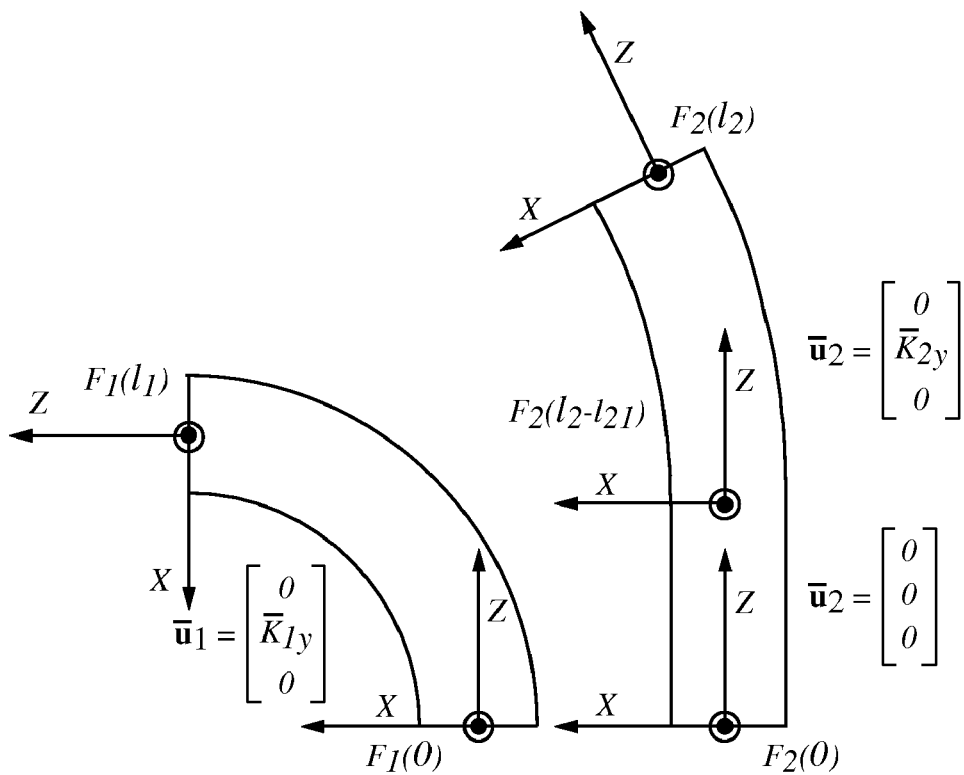
FIG. 8A illustrates a coordinate frame of an elongate member.

The members are labeled with subscript indices, i=1, 2, . . . , n, where 1 is the outermost elongate member and n is the innermost elongate member. As shown in FIG. 8A, a coordinate frame can be defined as a function of arc length s along elongate member i by defining a single frame at the insertion point, $F_i(0)$, such that its z axis is tangent to the elongate member's centerline. The frame, $F_i(s)$, is obtained by sliding $F_i(0)$ along the elongate member centerline without rotation about its z axis. Similarly, an insertion-point world frame, $W(0)$, is used to define a manipulator frame, $W(s)$, as a function of arc length. Superscripts will be used to indicate the coordinate frame of vectors and transforms.

Since the elongate members are assumed rigid in torsion, any relative rotation between the elongate members will be constant along their entire length. As the $i^{th}$ elongate member's coordinate frame $F_i(s)$ slides down its centerline, it experiences a body-frame angular rate of change per unit arc length given by $$\bar{u}_i^{F_i(s)}(s) = [\bar{\kappa}_{ix}, \bar{\kappa}_{iy}, \tau_i]^T \qquad (1)$$

in which $(\bar{\kappa}_{ix}, \bar{\kappa}_{iy})$ are the x and y components of curvature due to bending and $\tau_i = 0$ is the torsion. The over bars in (1) indicate values for the initial curvatures of the elongate members in their rest configurations. In the examples of FIG. 8A, the elongate members have nonzero y components of curvature in local frames, $F_i(s)$.

When the elongate members are assembled concentrically, the moment vector at any point along elongate member i is given by $$m_i^{F_i(s)}(s) = K_i (u_i^{F_i(s)}(s) - \bar{u}_i^{F_i(s)}(s)) \qquad (2)$$

in which $m_i^{F_i(s)}(s)$ is the moment vector, $u_i^{F_i(s)}(s)$ and $\bar{u}_i^{F_i(s)}(s)$ are the resultant and initial angular frame rates and $K_i$ is the frame-invariant stiffness tensor for a elongate member given by $$K_i = \begin{bmatrix} E_i I_i & 0 & 0 \\ 0 & E_i I_i & 0 \\ 0 & 0 & J_i G_i \end{bmatrix}. \qquad (3)$$

in which $E_i$ is the modulus of elasticity, $I_i$ is the area moment of inertia, $J_i$ is the polar moment of inertia, and $G_i$ is the shear modulus. For elongate members of cylindrical cross section, the area moment of inertia is given by $$I_i = (\pi/64)(d_o^4 - d_I^4)_i \qquad (4)$$

in which $d_I$ and $d_o$ are the inner and outer diameters of the cross section.

While (2) applies on a point-wise basis, the pure bending assumption permits it to be applied to sections of the manipulator in which each elongate member has constant initial curvature. The moment equilibrium equation can be applied to each of these sections by transforming (2) for each elongate member to the manipulator frame, $W(s)$. Defining $\theta_i$ as the z axis rotation angle from frame $W(s)$ to frame $F_i(s)$, the curvature vectors transform as $$\bar{u}_i^{W(s)} = R(z, \theta_i) \bar{u}_i^{F_i}. \qquad (5)$$

in which $R(z, \theta_i)$ is the rotation matrix. The moment equilibrium equation for the concentric elongate members is $$\sum_{i=1}^{n} m_i^{W(s)} = 0. \qquad (6)$$

Since all elongate members must conform to the same final curvature, $u_f^{W(s)}$, $$u_f^{W(s)} = u_1^{W(s)} = u_2^{W(s)} = \ldots = u_n^{W(s)} \quad (7)$$

Combining (2)-(7) yields an expression for the resultant angular frame rate for a section of manipulator length comprised of n overlapping elongate members of constant curvature, $$u_f^{W(s)} = \left(\sum_{i=1}^{n} K_i\right)^{-1} \sum_{i=1}^{n} K_i \bar{u}_i^{W(s)}. \quad (8)$$

Owing to the assumption of torsional rigidity, this expression takes the form $u_f^{W(s)} = [\kappa_{fx}, \kappa_{fy}, 0]^T$. The total moment applied to one elongate member by all the others can be interpreted as the vector sum of two bending moments—the moment necessary to remove its initial curvature $\bar{u}_i^{W(s)}$ and the moment necessary to produce its final curvature $u_f^{W(s)}$.

In one arrangement, the relative position of the distal end portion 40 of the manipulator 10 (e.g., relative to a proximal end portion of the manipulator 10), can be determined by mapping certain variables associated with the elongate members 12, 14, 16 to a frame of the distal end portion 40 of the manipulator 10 using a series of kinematic equations. The following outlines an example of the kinematic mapping process.

Figure 8B:
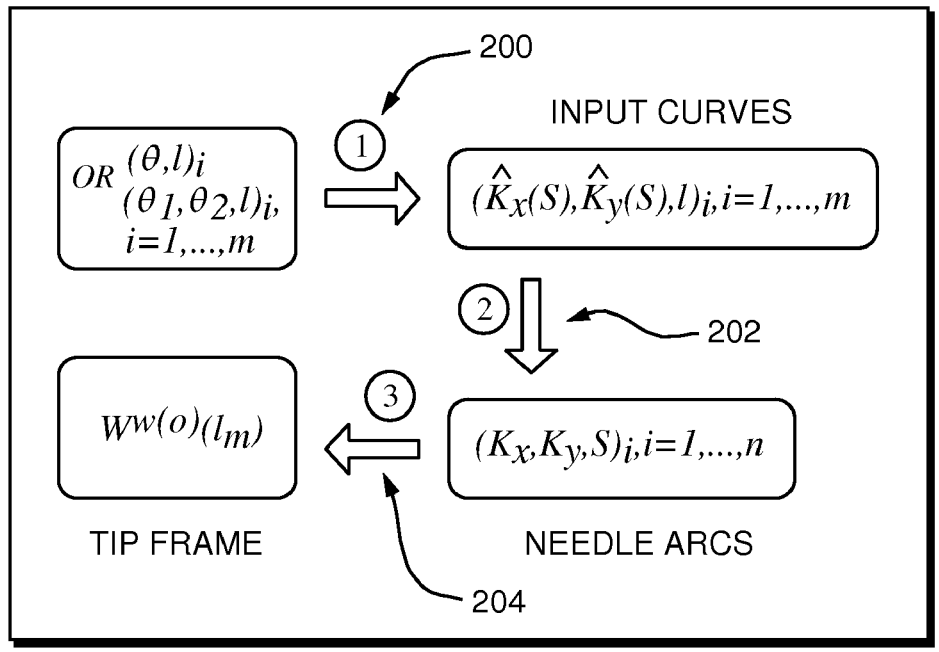
FIG. 8B illustrates kinematic mapping from elongate member variables to a distal end portion of a manipulator.

In one arrangement, kinematic mapping from elongate member variables to the distal end portion 40 of the manipulator 10 includes three mapping steps as diagrammed in FIG. 8B. The first mapping 200 converts the elongate member kinematic variables to m corresponding input curves of curvature $\hat{\kappa}_i(s) = [\hat{\kappa}_x(s) \, \hat{\kappa}_y(s)]_i$ and extension length, $l_i$. These m curves are of piecewise constant curvature. The second mapping 202 converts the input curves to the actual arcs of the manipulator, $(\kappa_x, \kappa_y, s)_j, j=1, \ldots, n$, where the number of arcs, n, is the total number of constant curvature segments for all the elongate members combined. These two mappings are considered separately because the designs of the individual elongate members are most easily described in the input curve space. This proves useful when computing the inverse kinematics. The third mapping 204 determines the manipulator tip coordinate frame, $W^{W(0)}(l_m)$, with respect to the manipulator base frame from the sequence of manipulator arcs.

The inverse kinematics problem involves solving for the elongate member kinematic variables that position the distal end portion 40 of the manipulator 10 at a desired spatial location and orientation. Solving this problem is important for both manipulator control and for surgical planning. One approach to solving the inverse kinematics problem includes sequentially inverting the three kinematic mappings described above.

Figure 4A:
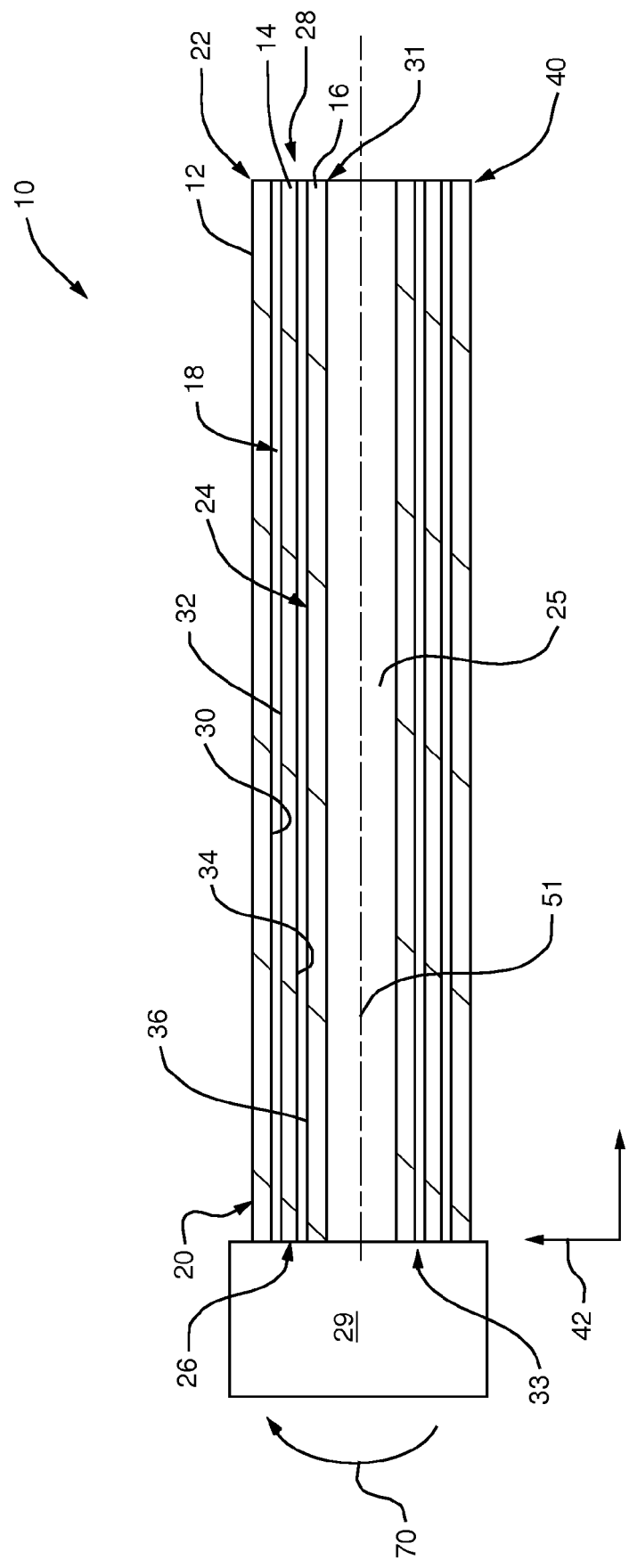
FIG. 4A illustrates a sectional view of an example manipulator having longitudinal axes substantially aligned with a reference axis.
Figure 4B:
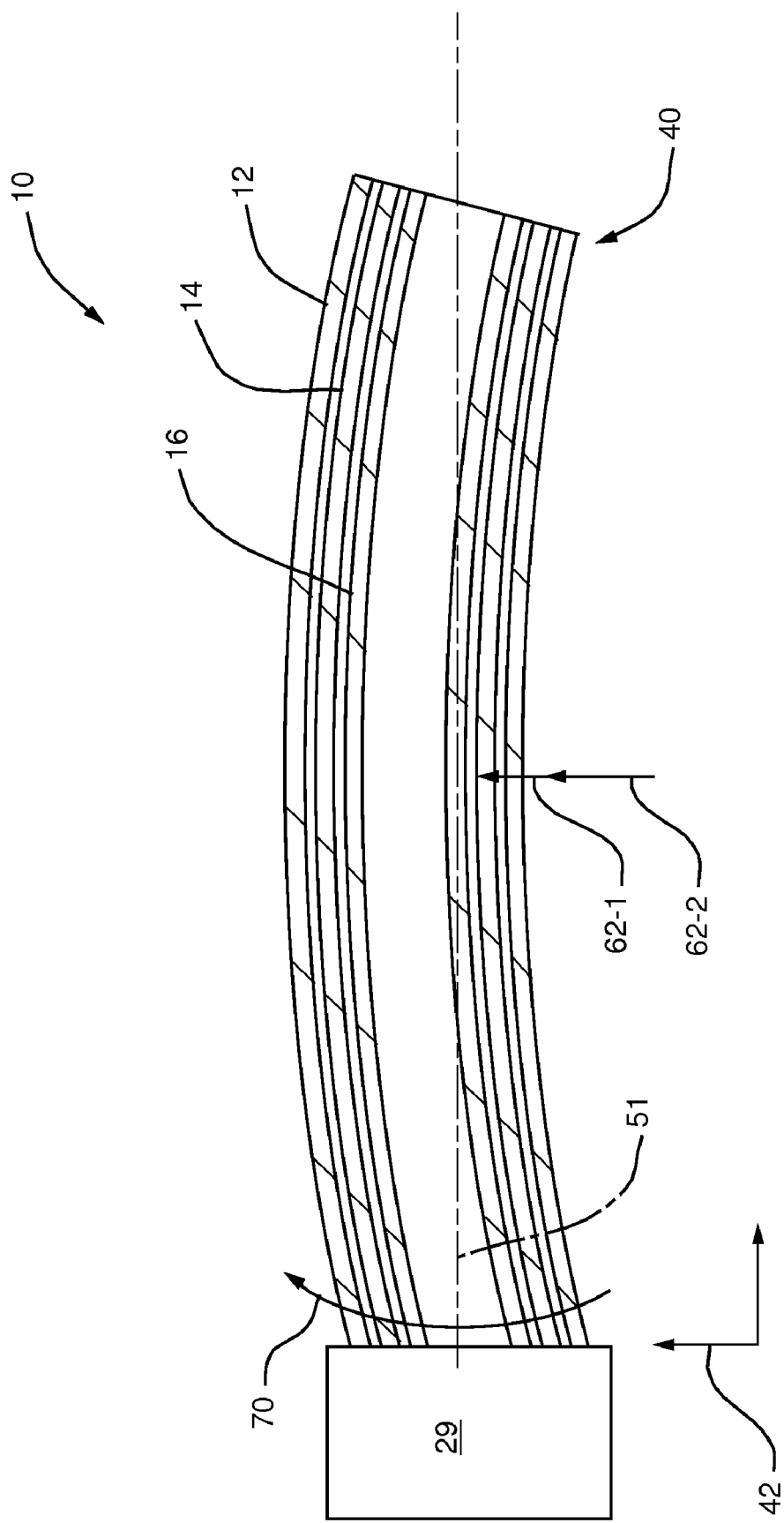
FIG. 4B is a sectional view of the manipulator of FIG. 4A illustrating a geometric configuration of the manipulator based upon the relative rotation of elongate members forming a balanced stiffness elongate member pair of the manipulator.
Figure 4C:
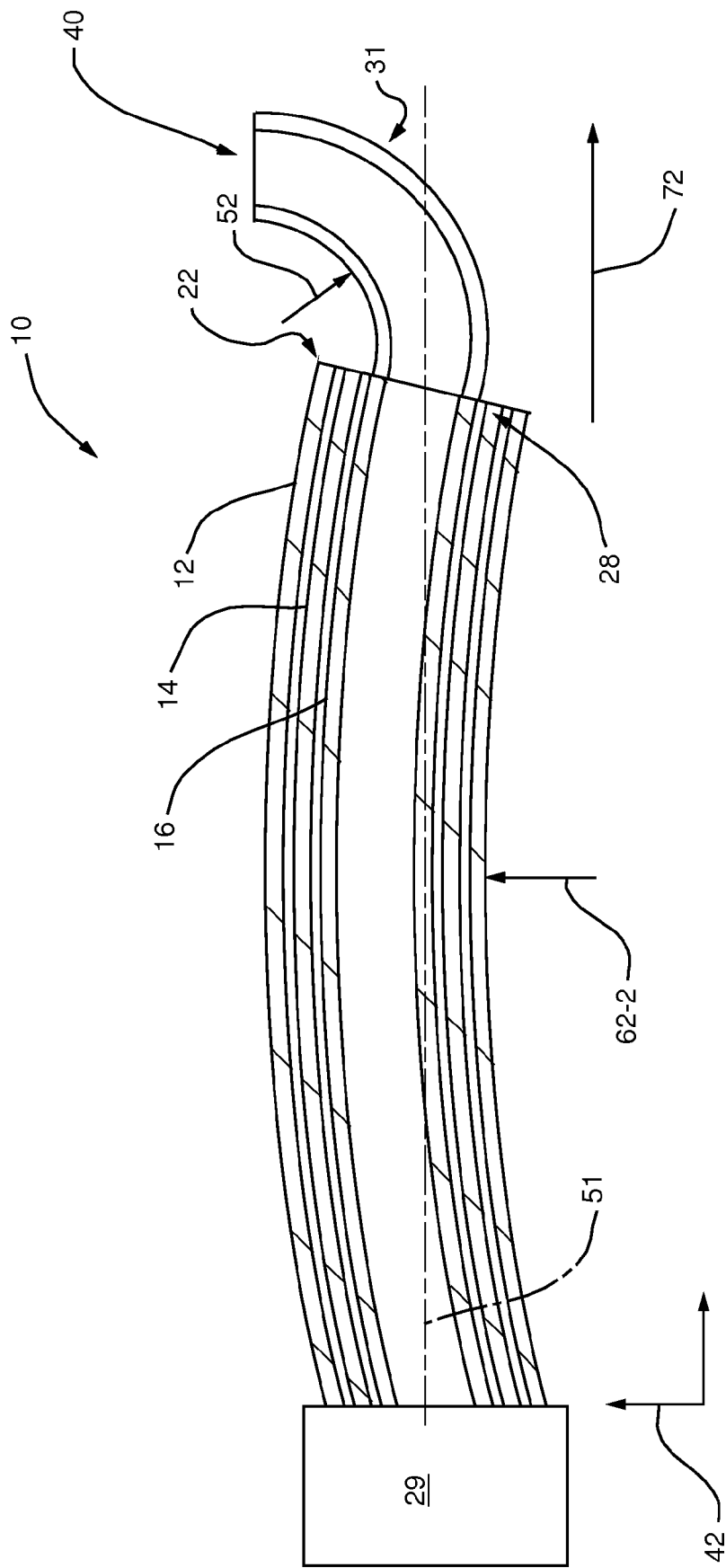
FIG. 4C is a sectional view of the manipulator of FIG. 4B illustrating a geometric configuration of the manipulator based upon the relative translation of elongate members forming a dominating stiffness elongate member pair of the manipulator.

As indicated above, the relative bending stiffness of sets of elongate members 12, 14, 16 can affect the positioning of the manipulator 10. In one example embodiment, the manipulator 10 can be configured to include a variety of combinations of balanced stiffness elongate member sets and dominating stiffness elongate member sets. FIGS. 4A through 4C illustrate one example configuration of the elongate members 12, 14, 16 of the manipulator 10, as well as the resulting positioning of the manipulator 10 based upon the relative rotation and translation of the elongate members 12, 14, 16.

FIGS. 4A through 4C illustrates a sectional view of an embodiment of the manipulator 10 having the first elongate member 12, the second elongate member 14, and the third elongate member 16 disposed in a concentric relationship. In the embodiment illustrated, assume that each of the first, second, and third elongate members are formed in a pre-curved or arcuate configuration. Also, further assume that the stiffness of the first elongate member 12 is substantially equal to a bending stiffness of the second elongate member 14 and the bending stiffness of the second elongate member is substantially greater than a bending stiffness of the third elongate member 16. With such a configuration, the first and second elongate members 12, 14 form a balanced stiffness elongate member set and the second and third elongate members 14, 16 form a dominating stiffness elongate member set.

In use, the elongate members 12, 14, 16 are rotated and/or translated, relative to the reference axis 51 to adjust a position of the distal end portion 40 of the manipulator 10 relative to the reference coordinate system 42. FIGS. 4A through 4C illustrate an example of this relative rotation and translation of the elongate members 12, 14, 16. Such rotation and translation of the elongate members 12, 14, 16 can be performed in a variety of ways. In one arrangement, the translation and rotation of the elongate members 12, 14, 16 can be manually controlled by a user. In another arrangement, the rotation and translation of the elongate members 12, 14, 16 can be controlled by one or more motorized devices, such as disposed within the housing 29.

In FIG. 4A, in a starting position, the elongate members 12, 14, 16 are relatively oriented such that the manipulator 10 is positioned in an extended position (e.g., non-rest configuration). For example, as indicated above, the first and second elongate members 12, 14 form a balanced stiffness elongate member set. As such, the first and second elongate members 12, 14 are relatively oriented such that the unstressed curvatures 61, 63 of the elongate members 12, 14 substantially oppose each other and the associated unstressed distal end portions 22, 28 orient in substantially opposing directions. Also, the second and third elongate members 14, 16 form a dominating stiffness elongate member set. As such, the third elongate member 16 is disposed within the second elongate member 14 such that the curvature of the third elongate member 16 conforms to the shape of the substantially stiffer second elongate member 14.

To adjust the position of the distal end portion of the manipulator, the first elongate member 12 can be rotated along direction 70, relative to the second elongate member 14, which is held in a substantially fixed position relative to the reference coordinate system 42, about the reference axis 51. As shown in FIG. 4B, because the first and second elongate members 12, 14 form a balanced stiffness elongate member set, rotation of the first elongate member 12 relative to the second elongate member 14 causes the first and second elongate members 12, 14 to bend relative to the reference coordinate system 42 where the bend has a radius of curvature 62-1. Furthermore, the second elongate member 14 and the third elongate member 16 form a dominating stiffness elongate member set. As such, the shape of the third elongate member 16 conforms to the bending of the second elongate member 14 such that the third elongate member 16 has a radius of curvature 62-2 that is substantially equal to the radius of curvature 62-1 of the second elongate member 14. As illustrated in FIG. 4B, bending of the first and second elongate members 12, 14 adjusts the position of the distal end portion 40 of the manipulator 10 relative to the reference coordinate system 42.

To further adjust the position of the distal end portion of the manipulator 10, as shown in FIG. 4C, the third elongate member 16 is translated along direction 72. As indicated above, the second elongate member 14 has a bending stiffness that is substantially greater than the bending stiffness of the third elongate member 16. As the third elongate member 16 is translated beyond the distal end portion 28 of the second elongate member 14, the third elongate member 16 returns to a relaxed state and assumes a pre-curved configuration, relative to the reference axis 51, having a radius of curvature 52. As a result, the relaxation of the third elongate member 16 adjusts the position of the distal end portion of the manipulator relative to the reference coordinate system 42 and allows a user to steer the distal end portion 40 of the manipulator 10 to a particular spatial location.

With respect to the example above, the first and second elongate members 12, 14 form a balanced stiffness elongate member set, the second and third elongate members 14, 16 form a dominating stiffness elongate member set. One of ordinary skill in the art will understand that other combinations are possible as well.

For example, in one arrangement, the first elongate member 12 has a bending stiffness that is substantially greater than a bending stiffness of the second elongate member 14 to form a dominating stiffness elongate member set while the second elongate member 14 has a bending stiffness that is substantially equal to a bending stiffness of the third elongate member 16 to form a balanced stiffness elongate member set. In another arrangement, the first elongate member 12 has a bending stiffness that is substantially equal to a bending stiffness of the second elongate member 14 to form a balanced stiffness elongate member set while the second elongate member 14 has a bending stiffness that is substantially equal to a bending stiffness of the third elongate member 16 to form a balanced stiffness elongate member set. In another arrangement, the first elongate member 12 has a bending stiffness that is substantially greater than a bending stiffness of the second elongate member 14 to form a first dominating stiffness elongate member set and the second elongate member 14 has a bending stiffness that is substantially greater than the bending stiffness of the third elongate member 16 to form a second dominating stiffness elongate member set. In yet another arrangement, the second elongate member has a bending stiffness that is substantially less than a bending stiffness of the third elongate member to form a dominating stiffness elongate member set and the first elongate member has a bending stiffness that is substantially less than a bending stiffness of the second elongate member to form a dominating stiffness elongate member set.

While the manipulator 10 can be configured to be applied in a variety of applications, in one arrangement, the manipulator is configured as a needle manipulator for use in percutaneous procedures. For example, returning to FIG. 1A, the elongate members 12, 14, 16 are configured to be inserted into a tissue region of interest. As such, the outer diameter of the elongate members 12, 14, 16 have outer diameters that range between approximately 2.0 mm (e.g., the outer diameter of the first elongate member 12) to about 0.7 mm (e.g., the outer diameter of the third elongate member 16).

The needle manipulator 10 can be configured to be inserted into a tissue region of interest in a variety of ways. In one arrangement, at least one elongate member 12, 14, 16 is configured as a needle operable to introduce the manipulator into a tissue site (e.g., percutaneous insertion). For example, a pointed stylet can be disposed within the third elongate member 16 and used to pierce a tissue to introduce the manipulator 10 into a tissue site. In another example, while not illustrated in FIG. 1A, the first elongate member 12 can be pointed or beveled to allow the needle manipulator 10 to pierce a tissue to introduce the manipulator 10 into a tissue site. In another arrangement, the distal end portion 40 of the needle manipulator is substantially blunt to allow insertion of the needle manipulator 10 into a tissue location through a body orifice (e.g., nasal canal). In another arrangement, the elongate members 12, 14, 16 can be disposed within a sheath 110 configured to introduce the needle manipulator into a tissue site. For example, the sheath 110, such as a cannula, can be inserted into a tissue site to aid in directing the needle manipulator 10 to a tissue location. While the sheath 110 is shown as forming part of the housing 29, one of ordinary skill in the art will understand that the sheath 110 can be formed separately from the housing.

Figure 6:
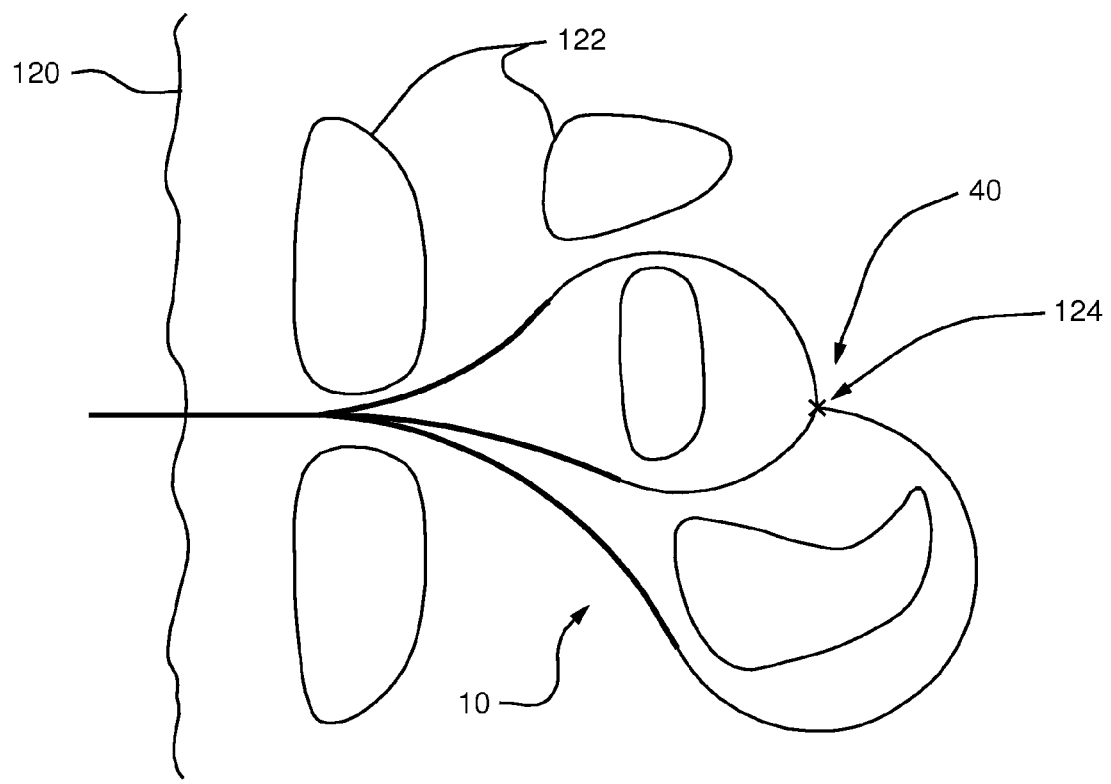
FIG. 6 illustrates use of the manipulator of FIG. 1A as a needle manipulator inserted in a percutaneous location.
Figure 7:
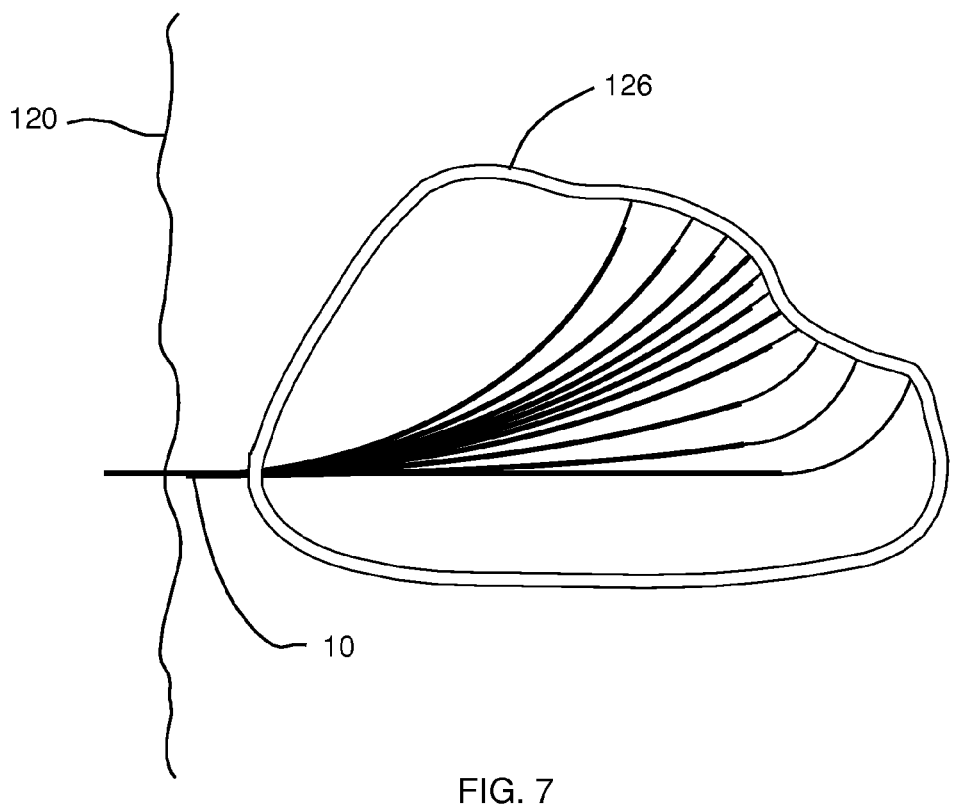
FIG. 7 illustrates the use of the manipulator of FIG. 1A as a needle manipulator inserted within a body lumen.

In use, the relative rotation and translation of the elongate members 12, 14, 16, as described above, allows a user to position the distal end portion 40 of the needle manipulator 10 to a desired tissue location. For example, as shown in FIG. 6, as the needle manipulator 10 is inserted within a tissue 120, the user can relatively rotate and translate the elongate members 12, 14, 16 to steer the distal end portion 40 of the needle manipulator 10 to avoid obstacles 122, such as bone or delicate tissue, as the distal end portion 40 of the needle manipulator 10 is advanced to a tissue location 124. Also, as indicated in FIG. 7, the needle manipulator 10 does not rely on tissue interaction to determine its geometric configuration. For example, by relatively rotating and translating of the elongate members 12, 14, 16, a user can position the distal end portion 40 of the needle manipulator at various locations within a body lumen 126.

Returning to FIG. 1A, the needle manipulator 10, in one arrangement, is configured to deliver a tool or prosthetic device to a surgical site. For example, in one arrangement as shown in FIG. 4A, the third elongate member 16 is configured with a third elongate member lumen 25 extending between a proximal end portion 33 and the distal end portion 31. As shown in FIG. 1A, the third elongate member 16 includes a surgical tool 130 disposed within the lumen 25. The surgical tool 130 can have a variety of different configurations. For example, as shown in FIG. 1A the surgical tool 130 can be configured as a balloon catheter 130.

While this invention has been particularly shown and described with references to preferred embodiments thereof, it will be understood by those skilled in the art that various changes in form and details may be made therein without departing from the spirit and scope of the invention as defined by the appended claims.

As indicated above, in one embodiment, each of the elongate members 12, 14, 16 is formed as having a preset curved shape when in a resting state. Such description is by way of example only. In one arrangement, at least one of the elongate members is configured in a generally extended shape when in a resting state. For example, the first elongate member 12 can be formed from a substantially rigid material having a lumen extending along a longitudinal axis of the first elongate member 12. In such a configuration, the first elongate member can operate as a sheath or an introducer to introduce the manipulator 10 into a tissue region.

Additionally, as described above, while the elongate members 12, 14, 16 can be formed as having a preset curved shape when in a resting state, the curvature along the length of one or more elongate members 12, 14, 16 need not be continuous, but is also considered as a preset curved shape. For example, while FIG. 1C depicts a case in which the elongate member 14 has two regions of constant curvature, in practice, such an elongate member 14 can consist of any number of separately curved sections. Furthermore, the curvature can be variable within each section.

Also, as described above, the first elongate member 12 defines a first elongate member lumen 18 having a substantially circular and constant-area cross-sectional shape and that extends between a proximal end portion 20 and a distal end portion 22 with the second elongate member 14 being disposed within the first elongate member lumen 18. Such description is by way of example only. The elongate members 12, 14, 16 can have a variety of cross-sectional shapes that also vary along their length. For example, the elongate members 12, 14, 16 can have asymmetric cross-sectional shapes so that their bending stiffness varies with the choice of cross-sectional axis. The cross-sectional shapes can also vary along the length of an elongate member in a continuous or discontinuous manner producing consequent changes in bending stiffness along the length of the elongate member. Cross-sectional shape variations can also produce variations in the gap formed between the outer surface of a second elongate member 14 (e.g., an inner elongate member) and the inner surface of a first elongate member 12 (e.g., an outer elongate member) in which the second elongate member 14 is inserted.

Figure 9:
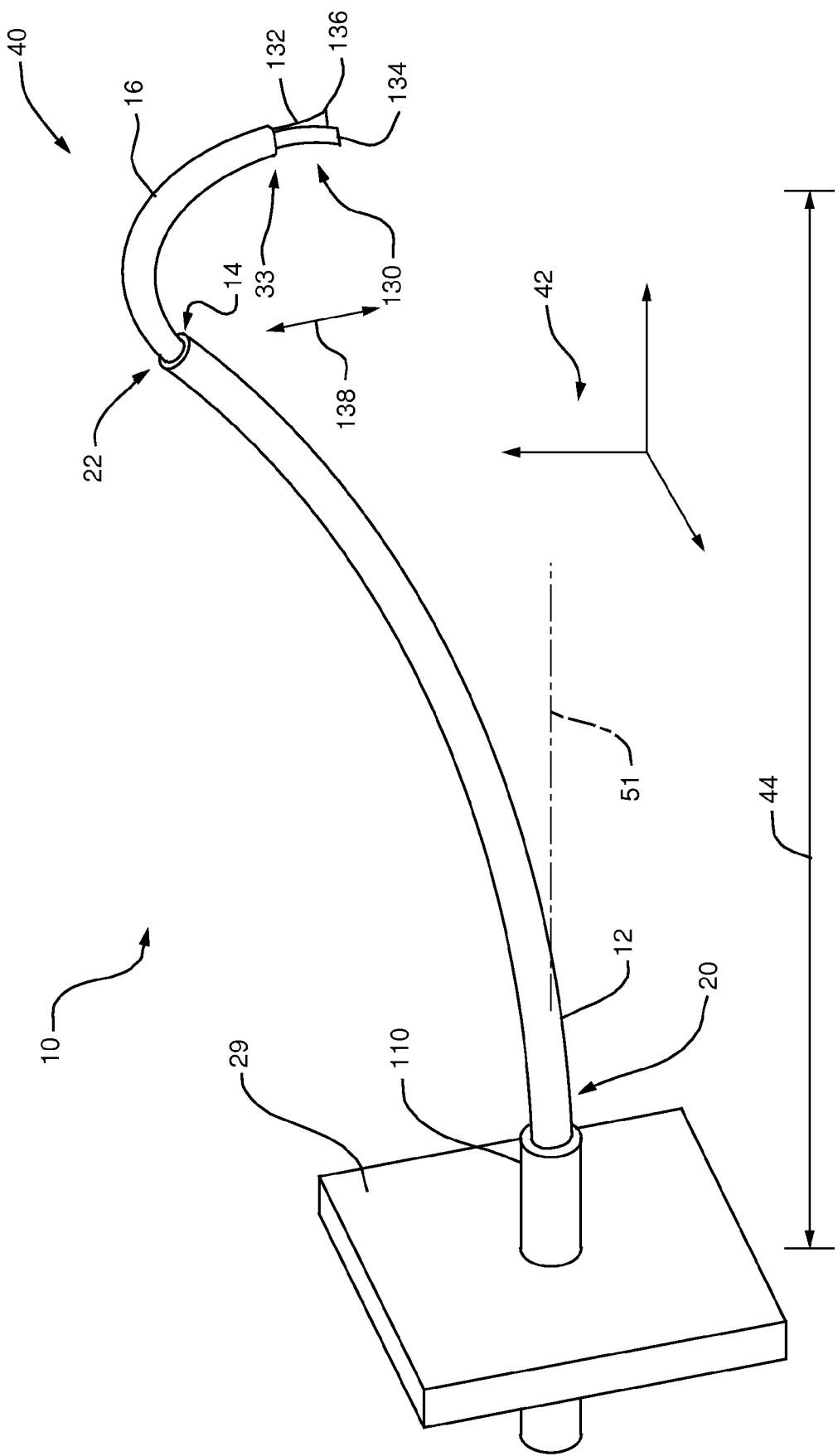
FIG. 9 illustrates an example of a manipulator.

As described with respect to FIG. 1A, the third elongate member 16 can include a surgical tool 130 disposed within the lumen 25. The surgical tool 130 can have a variety of different configurations. As shown in FIG. 9, the surgical tool 130 is configured as a tissue grasping device 132. In one arrangement, the tissue grasping device 132 is formed from a shape-memory material, such as Nitinol, having a first arm 134 and an opposing second arm 136. In a resting position, the first and second arms 134, 136 are disposed in an open relationship such that the first and second arms 134, 136 extend away from each other, such as when the tissue grasping device 132 extends beyond the distal end portion 33 of the third elongate member 16. In use, relative translation of the tissue grasping device 132 and the third elongate member 16, along an axis 138, position the tissue grasping device 132 between the resting position as shown and a collapsed or closed position in which the first arm 134 and the second arm 136 are disposed in proximity to each other.

What is claimed is:

1. A manipulator, comprising:
   at least three elongate members disposed in a moveable relationship and in a substantially concentric relationship relative to each other; and
   at least one elongate member of the at least three elongate members configurable, within an elastic range, between a rest configuration in which at least a portion of the at least one elongate member of the at least three elongate members has a first curvature relative to a reference axis and a non-rest configuration in which at least the portion of the at least one elongate member of the at least three elongate members has a second curvature different from the first curvature relative to the reference axis;
   wherein at least one pair of the elongate members have a stiffness relationship that is a non-dominant stiffness relationship characterized by one elongate member of the pair having a bending stiffness that is neither substantially greater than nor substantially less than a bending stiffness of the other elongate member of the pair,
   the first set of elongate members of the at least three elongate members being configured to be positioned between the non-rest configuration and the rest configuration in response to relative displacement between a first elongate member of the first set of elongate members and a second elongate member of the first set of elongate members, and the second set of elongate members of the at least three elongate members configured to be positioned between the non-rest configuration and the rest configuration in response to relative displacement between a first elongate member of the second set of elongate members and a second elongate member of the second set of elongate members,
   each of the sets of elongate members comprises the respective first and second elongate members having a stiffness relationship selected from the group consisting of a dominant stiffness relationship and a balanced stiffness relationship, the dominant stiffness relationship being characterized by the first elongate member having a bending stiffness that is substantially greater than a bending stiffness of the second elongate member, the balanced stiffness relationship being characterized by the first elongate member having a bending stiffness that is substantially equal to a bending stiffness of the second elongate member,
   the first set of elongate members having the balanced stiffness relationship, and a distal end portion of the first elongate member of the first set and a distal end portion the second elongate member of the first set being configured to be positioned between the non-rest configuration and the rest configuration in response to relative rotation between the first elongate member and the second elongate member of the first set about the reference axis, and
   the second set of elongate members having the dominant stiffness relationship, and a distal end portion of the first elongate member of the second set being configured to be positioned between the non-rest configuration and the rest configuration in response to relative translation between the first and second elongate members of the second set along the reference axis,
   and the at least three elongate members are configured such that relative displacement of the at least three elongate members adjusts a spatial position of a distal end of the manipulator.

2. The manipulator of claim 1, wherein a surgical tool or device is attached to a distal end portion of an elongate member or is deployed through an elongate member lumen extending between proximal and distal end portions of the elongate member.

3. The manipulator of claim 1, wherein:
   one of the elongate members defines a lumen having a substantially circular cross-sectional shape, the lumen extending between a proximal end portion and a distal end portion of the elongate member.

4. The manipulator of claim 1, wherein:
   one of the elongate members defines a substantially asymmetric cross-sectional shape along a length of the elongate member.

5. The manipulator of claim 1, wherein
   one of the elongate members has a substantially variable cross sectional shape and/or area extending along the length of the elongate member.

6. The manipulator of claim 1, wherein:
   for one of the sets of elongate members, a respective first elongate member of the set is substantially stiffer than a respective outer second elongate member of the set.

7. The manipulator of claim 1, wherein the first curvature is a variable curvature varying along the length of the portion of the at least one elongate member of the at least three elongate members.

8. The manipulator of claim 1 wherein the material composition of one or more of the elongate members varies along its length.

9. The manipulator of claim 1, configured for use in therapy.

10. The manipulator of claim 1, wherein at least one elongate member of the at least three elongate members is configured as a needle operable to introduce the manipulator into a tissue location.

11. The manipulator of claim 1, further comprising a sheath, the at least three elongate members disposed within the sheath.

* * * * *